(12) United States Patent
Bhatia et al.

(10) Patent No.: US 6,410,003 B1
(45) Date of Patent: Jun. 25, 2002

(54) ANTIPERSPIRANT COMPOSITIONS

(75) Inventors: Shameem Bhatia; Kevin Ronald Franklin, both of Bebington; Lara Dimitrova Stoimenof, London; Michael Stephen White, Bebington, all of (GB)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/920,777

(22) Filed: Aug. 2, 2001

(30) Foreign Application Priority Data

Aug. 4, 2000 (GB) .............................. 0019231

(51) Int. Cl.$^7$ .............................. A61K 7/32; A61K 7/34; A61K 7/38; A61K 7/00
(52) U.S. Cl. .............................. 424/65; 424/66; 424/68; 424/400; 424/401
(58) Field of Search .............................. 424/65, 66, 68, 424/400, 401

(56) References Cited

U.S. PATENT DOCUMENTS

| | | | | |
|---|---|---|---|---|
| 3,969,087 A | * | 7/1976 | Saito et al. .................. | 252/316 |
| 4,293,544 A | | 10/1981 | Elmi .............................. | 424/60 |
| 4,725,430 A | * | 2/1988 | Schamper et al. ............ | 424/65 |
| 4,725,432 A | | 2/1988 | May .............................. | 424/66 |
| 4,822,602 A | * | 4/1989 | Sabatelli ...................... | 424/65 |
| 4,954,333 A | * | 9/1990 | Ward ............................ | 424/66 |
| 5,169,626 A | | 12/1992 | Tanner et al. ................. | 424/66 |
| 5,750,096 A | * | 5/1998 | Guskey et al. ................ | 424/65 |
| 5,972,319 A | | 10/1999 | Linn et al. .................... | 424/65 |

FOREIGN PATENT DOCUMENTS

| | | |
|---|---|---|
| EP | 0 512 770 | 11/1992 |
| WO | 91/04009 | 4/1991 |
| WO | 92/19222 | 11/1992 |
| WO | 97/16163 | 5/1997 |
| WO | 98/27954 | 7/1998 |

OTHER PUBLICATIONS

PCT International Search Report in a PCT application PCT/GB 01/02882.
GB Search Report in a GB application GB 0019231.0.
Cosmetics & Toiletries, *"Deodorant/Antiperspirant —Sticks"*, 1990, vol. 105, pp. 75–78.
Angew. Chem. Int. Ed. Engl. 1996, 35, *"Prominent Gelation and Chiral Aggregation of Alkylamides Derived from trans–1,2–Diaminocyclohexane"*, p. 1949.
Derwent Abstract of JP 10–237034, published Sep. 8, 1998.

* cited by examiner

*Primary Examiner*—Shelley A. Dodson
(74) *Attorney, Agent, or Firm*—Kevin J. Stein

(57) ABSTRACT

Antiperspirant formulations containing an antiperspirant active and a continuous phase comprising a water-immiscible liquid carrier, such as, amongst other materials, cyclomethicones, that is structured using an amido-containing compound of the general formula

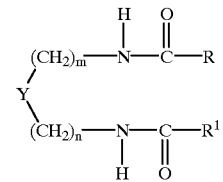

in which R and R$^1$ each independently denote a branched or unbranched moiety containing 5 to 27 carbon atoms, m and n are each independently, zero or 1, Y is a cyclohexane ring bearing the amido-containing substituent groups

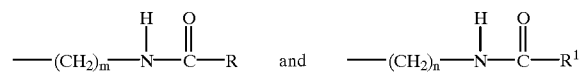

in 1,2 or 1,3 positions.

32 Claims, No Drawings

ANTIPERSPIRANT COMPOSITIONS

FIELD OF THE INVENTION

The present invention relates to antiperspirant compositions for application to human skin, especially the axilla.

BACKGROUND OF THE INVENTION AND SUMMARY OF PRIOR ART

A wide variety of cosmetic compositions for application to human skin make use of a thickened or structured liquid carrier to deliver colour or some other active material to the surface of the skin. A significant example of such cosmetic compositions are antiperspirant compositions which are widely used in order to enable their users to avoid or minimise wet patches on their skin, especially in axillary regions.

Antiperspirant formulations have been provided with a range of different product forms. One of these is a so-called "stick" which is usually a bar of an apparently firm solid material held within a dispensing container and which retains its structural integrity and shape whilst being applied. When a portion of the stick is drawn across the skin surface a film of the stick composition is transferred to the skin surface. Although the stick has the appearance of a solid article capable of retaining its own shape for a period of time, the material usually has a structured liquid phase so that a film of the composition is readily transferred from the stick to another surface upon contact.

Another possibility is that a stick is a softer solid composition accommodated in a dispensing container which in use extrudes the composition through one or more apertures.

Antiperspirant sticks can be divided into three categories. Suspension sticks contain a particulate antiperspirant active material suspended in a structured carrier liquid phase which generally is water-immiscible and may be anhydrous. Emulsion sticks normally have a hydrophilic phase containing the antiperspirant active in solution, this phase forming an emulsion with a second, more hydrophobic, liquid phase. The continuous phase of the emulsion is structured. Solution sticks typically have the antiperspirant active dissolved in a structured liquid phase which is polar and may be a mixture of water and a water-miscible organic solvent, or may be polar organic solvent without water. This classification into suspension, emulsion and solution types can be applied to both firm and soft solid compositions.

There is substantial literature on the structuring or thickening of antiperspirant compositions.

Conventionally, many sticks have been structured using naturally-occurring or synthetic waxy materials. In this way, it is possible to obtain either a soft solid or a firm solid. Examples of wax-structured sticks are described in an article in Cosmetics and Toiletries, 1990, Vol 105, P75–78 and in U.S. Pat. Nos. 5,169,626 and 4,725,432.

More specifically it has been common practice for sticks to be structured by incorporating fatty alcohol into the composition, often accompanied by a smaller amount of castor wax. Sticks which are structured with fatty alcohol tend to leave visible white deposits on application to human skin; moreover the deposits can also transfer onto clothing when it comes into contact with the skin and the wearer can, for example, find white marks at the armhole of the sleeveless garment. Fatty alcohols are often regarded as coming within the general category of waxy materials, but we have observed that they are a more significant source of white deposits than other waxy materials.

Some alternative structurants have been proposed. The term "gellant" is often employed instead of "structurant". Where the resulting product is liquid of increased viscosity rather than a solid or gel, the term "thickener" can also be used. For example, the use of dibenzylidene sorbitol (DBS) or derivatives thereof as gellant has been proposed in a number of publications such as EP-A-512770, WO 92/19222, U.S. Pat. Nos. 4,954,333, 4,822,602 and 4,725, 430. Formulations containing such gellants can suffer from a number of disadvantages, including instability in the presence of acidic antiperspirants, and comparatively high processing temperatures needed in the production of sticks.

U.S. Pat. No. 5,750,096 is one of several documents which teaches that gelation can be brought about using esters or amides of 12-hydroxystearic acid. The alcohol used to form such an ester or the amine used to form such an amide may contain an aliphatic, cycloaliphatic or aromatic group with up to 22 carbons therein. If the group is aliphatic it preferably contains at least three carbon atoms. A cycloaliphatic group preferably contains at least five carbon atoms and may be a fixed ring system such as adamantyl.

N-acyl amino acid amides and esters are also known to structure liquids. We have established that they do so by forming fibrous networks. They are described in U.S. Pat. No. 3,969,087. N-Lauroyl-L-glutamic acid di-n-butylamide is commercially available from Ajinomoto under their designation GP-1.

Further materials which have been disclosed as gelling agents are the amide derivatives of di and tribasic carboxylic acids set forth in WO 98/27954 notably alkyl N,N'-dialkyl succinamides.

It is known from Hanabusa et al "Prominent Gelation and Chiral Aggregation of Alkylamides Derived from Trans 1,2 Diaminocyclohexane" published in Angew. Chem. Int. Ed. Engl. 1996 35, page 1949 that alkylamides derived from trans-1,2-diaminocyclohexane are capable of causing the gelation of a number of organic liquids. The authors reported that the corresponding cis-compound did not bring about gelation of any of the liquids tested. Moreover, use of an optically active form of the trans-compound was necessary because the racemic form was found to give only an unstable gel.

Japanese published patent application JP-A-10-237034 (Polar Kasei Kogyo KK, inventors Hanabusa et al) discloses cosmetic compositions containing an organic oil gelled with such derivatives of 1,2-diaminocyclohexane.

WO 91/04009 (Gillette) discloses antiperspirant compositions containing dioctyl cyclohexane, but that material is a liquid present to prevent phase separation of the masking agent and does not function as a gellant.

SUMMARY OF THE INVENTION

We have now found that selected 1,2- and 1,3-substituted cyclohexane derivatives can be used as structurants for antiperspirant compositions. When used as a modest percentage of the composition, typically not more than 15% by weight and often less than 10% by weight, they are able to structure the composition, yet at the same time the composition gives a deposit with a low visible residue.

It is an object of the present invention to provide structured antiperspirant compositions, in which a liquid carrier material is thickened or structured using a structuring agent which is different from those mentioned above. A further object of the invention is to provide a structurant which can have superior properties to at least some of the structurants which have been used previously.

A yet further object of some embodiments of the invention is to provide compositions which exhibit low visible deposits.

Broadly, a first aspect of the present invention provides an antiperspirant composition comprising:
(i) a continuous phase which comprises water-immiscible liquid carrier,
(ii) a structurant therein which is at least one amido-containing compound of the general formula

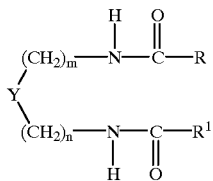

wherein R and $R^1$ each independently denote a branched or unbranched moiety containing 5 to 27 carbon atoms, m and n are each independently, zero or 1, Y is a cyclohexane ring bearing the amido-containing substituent groups

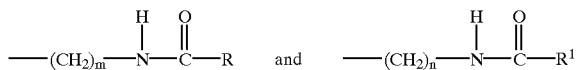

in 1,2 or 1,3 positions; and
(iii) an antiperspirant active material.

Each aliphatic group R or $R^1$ may be an unsubstituted alkyl or an alkenyl group, or it may bear functional substituents which incorporate hetero atoms such as oxygen or nitrogen, or it may include hetero atoms in a linkage in the chain. If hetero atoms are present they may, desirably, be included in groups able to participate in hydrogen bonding.

R and $R^1$ may, independently of each other, contain 11 to 17 carbon atoms. They may be mixed groups such as an aliphatic chain with an aromatic group or cycloalkyl group embedded in it.

If Y is a cyclohexane ring bearing the substituent groups in 1,3-positions, m and n are preferably 1. If Y bears the substituents groups in 1,2-positions m and n are preferably zero.

An amido-containing compound as above serves as a structuring agent or thickener for the water-immiscible liquid carrier and when used in a sufficient amount, which is likely to be less than 15% of the total composition, is able to structure this liquid into a gel with sufficient rigidity to sustain its own shape.

We have observed that the structuring compounds used in this invention form fibres or strands within the liquid phase.

Without being bound to any specific theory or explanation, we believe that upon gel formation a network of such fibres is formed which extends throughout the liquid phase. Upon heating the gel to the gel melting temperature, the strands of structurant dissolve and the liquid phase becomes more mobile.

In order to promote good sensory properties at the time of use it is preferred to include silicone oil in the water-immiscible carrier liquid. The amount of silicone oil may be at least 10% by weight of the composition and/or at least 40% by weight of the water-immiscible carrier liquid.

Ethanol gives a cooling effect on application to skin, because it is very volatile. It is preferred that the content of ethanol or any monohydric alcohol with a vapour pressure above 1.3kPa (10 mmHg) is not over 15% better not over 8% by weight of the composition.

Fatty alcohols which are solid at room temperature of 20° C., such as stearyl alcohol, lead to deposits with an opaque white appearance and are preferably kept to low concentration or entirely excluded. As already mentioned, fatty alcohols are often regarded as coming within the general category of waxy materials. More generally the term "wax" is conventionally applied to a variety of materials and mixtures (including some fatty alcohols) which have some diversity in chemical structure but similarity in physical properties. The term generally denotes materials which are solid at 30° C., often also solid up to 40° C., but which melt to a mobile liquid at a temperature below 95° C. usually below 90° C.

Possibly the composition does not include more than 3% of any material which is solid at 30° C. but at 95° C. is molten and soluble in the water-immiscible liquid of the continuous phase, yet which is unable to form a network of fibres in the continuous phase on cooling to 20° C.

As will be explained in more detail below, the structured water-immiscible carrier liquid may be the continuous phase of a composition with a dispersed second phase, either an emulsion or a suspension of particulate solid. Such a solid may be a particulate antiperspirant active. A disperse phase may be a solution of antiperspirant active in water or other hydrophilic solvent.

Further advantages of preferred structurant materials of this invention are that they do not require high processing temperatures and that they are chemically stable, both during processing and in the resultant compositions. The avoidance of high processing temperatures can be especially valuable when the composition contains some water or other volatile constituent.

A composition of this invention will generally be marketed in a container by means of which it can be applied at time of use. This container may be of conventional type.

A second aspect of the invention therefore provides an antiperspirant product comprising a dispensing container having at least one aperture for delivery of the contents of the container, means for urging the contents of the container to the said aperture or apertures, and a composition of the first aspect of the invention in the container.

Means for urging the contents of the container to the said aperture or apertures, for flow through them, may be moving parts operable by the user.

However, if the composition is a soft solid, means for urging the contents of the container to the said aperture or apertures, may simply be flexible container walls so that the user can expel composition from the container by squeezing it.

The compositions of this invention can be produced by conventional processes for making cosmetic solids or soft-solids.

Thus, according to a third aspect of the present invention there is provided a process for the production of an antiperspirant composition comprising, not necessarily in any order, the steps of:
incorporating into a water-immiscible liquid carrier a structurant which is one or more structurant compounds as defined above, mixing the liquid carrier with a solid or a disperse liquid phase comprising antiperspirant active in particulate or dissolved form to be suspended therein, and which comprises an antiperspirant active,
heating the liquid carrier or a mixture containing it to an elevated temperature at which the structurant is soluble in the water-immiscible liquid carrier, followed by:
introducing the mixture into a mould which preferably is a dispensing container, and then cooling or permitting the mixture to cool to a temperature at which it is thickened or solidified.

A suspended solid may be an antiperspirant active and a disperse liquid phase may be a solution of such an active in a hydrophilic or polar solvent.

According to a fourth aspect of the present invention, there is provided a cosmetic method for preventing or reducing perspiration on human skin comprising topically applying to the skin a composition comprising an antiperspirant active, a water-immiscible liquid carrier and a structurant compound as defined above.

DETAILED DESCRIPTION AND EMBODIMENTS

As mentioned above the invention requires a structurant compound within a water-immiscible liquid phase. Other materials may also be present depending on the nature of the composition. The various materials will now be discussed by turn and preferred features and possibilities will be indicated.

The structurant compounds of the present invention have a general formula:

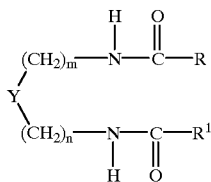

as given above. Two more specific possibilities are:

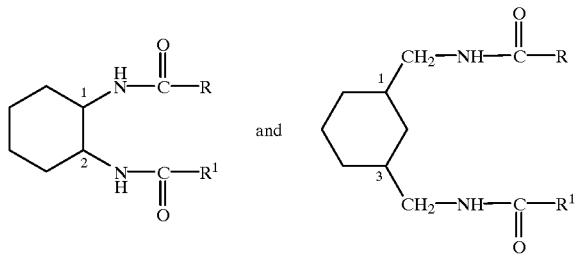

In the above formulae R and $R^1$ are preferably the same.

In the formulae above the two ring carbon atoms (shown numbered) bonded to the amido group-containing side chains are both chiral centres. The compounds thus have the possibility of more than one stereochemical conformation of the aliphatic ring and also optical enantiomers of each stereochemical form.

We have found that all stereochemical and optical isomers will function as structurants, although optically active forms may be superior.

The amido-containing structurant compound(s) used in this invention may be a mixture of compounds within the general formulae given, or may be a single compound, possibly as a mixture of its optically active forms.

These amido-containing structurant compounds can be prepared by reacting the respective amine compound with an acid chloride, or possibly with an anhydride or an ester.

The amount of the said structurant compound(s) in a composition of this invention is likely to be from 0.1 or 0.5 to 15% by weight of the whole composition and preferably from 0.5 up to 8% or 10%, probably from 1 to 8%. In other instances, the amount is from 10 to 15% of the formulation.

If the composition is an emulsion with a separate disperse phase, the amount of structurant compound(s) is likely to be from 0.5 to 20% or even 25% by weight of the continuous phase, more likely from 1% to 15% of this phase.

Carrier Liquid

The water-immiscible carrier liquid comprises one or a mixture of materials which are relatively hydrophobic so as to be immiscible in water. Some hydrophilic liquid may be included in the carrier, provided the overall carrier liquid mixture is immiscible with water. It will generally be desired that this carrier is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ $m^2$/sec (10 centistokes), and particularly above $10^{-7}$ $m^2$/sec (0.1 centistokes), the linear siloxanes normally exhibiting a viscosity of below $5\times10^{-6}$ $m^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid carrier may contain from 0% to 100% by weight of one or more liquid silicones. Preferably, there is sufficient liquid silicone to provide at least 10%, better at least 15%, by weight of the whole composition. If silicone oil is used, volatile silicone preferably constitutes from 20 to 100% of the weight of the carrier liquid. In many instances, when a non-volatile silicone oil is present, its weight ratio to volatile silicone oil is chosen in the range of from 1:3 to 1:40.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers are liquid aliphatic or aromatic esters, but these can be used as only part of the liquid carrier, desirably not above 20%, and possibly less than 10% by weight of the water-immiscible liquid carrier.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

Further instances of suitable hydrophobic carriers comprise liquid aliphatic ethers derived from at least one fatty alcohol, such as myristyl ether derivatives e.g. PPG-3 myristyl ether or lower alkyl ethers of polygylcols such as PPG-14 butyl ether.

Aliphatic alcohols which are solid at 20° C., such as stearyl alcohol are preferably absent or present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Silicon-free liquids can constitute from 0–100% of the water-immiscible liquid carrier, but it is preferred that silicone oil is present and that the amount of silicon-free constituents preferably constitutes up to 50 or 60% and in many instances from 20 to 60% by weight of the carrier liquid.

Liquid Disperse Phase

If the composition is an emulsion in which the amido-containing compound acts as a structurant in the continuous phase, the emulsion will contain a more polar disperse phase. The disperse phase may be a solution of an active ingredient.

The hydrophilic disperse phase in an emulsion normally comprises water as solvent and can comprise one or more water soluble or water miscible liquids in addition to or replacement for water. The proportion of water in an emulsion according to the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion the disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with high proportion of disperse phase, i.e. from 65 to 85% disperse phase, may also be advantageous. They can give good hardness even though the concentration of structurant may be only a small percentage of the total composition.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10–25, steareth-10–25 (i.e. $C_{16}$ to $C_{18}$ alcohols ethoxylated with 10 to 25 ethylene oxide residues) and PEG-15–25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™T, Pluronic™, Prisorine™, Quest PGPH™, Span™, Tween™, SF1228, DC$_{3225}$C and Q2–5200.

Antiperspirant Actives

The composition will also contain an antiperspirant active. Antiperspirant actives, are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)$ COOH.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active. However, when the active salt is in solution, its weight excludes any water present.

If the composition is in the form of an emulsion the antiperspirant active will be dissolved in the disperse phase. In this case, the antiperspirant active will often provide from 3 to 60% by weight of the disperse phase, particularly from 10% or 20% up to 55% or 60% of that phase. Alternatively, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 $\mu$m with a mean particle size often from 3 to 20 $\mu$m. Both larger and smaller mean particle sizes can also be contemplated such as from 20 to 50 $\mu$m or 0.1 to 3 $\mu$m.

Optional Ingredients

Optional ingredients in compositions of this invention can include disinfectants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Tricloban™, and Chlorhexidine warrant specific mention. A yet another class comprises biguanide salts such as are available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

A further optional constituent of the formulation comprises one or more secondary structurants which can be employed in addition to the amido-containing compound which is the primary structurant. The amount of such secondary structurants in the formulation is often zero, and usually not more than 15% of the formulation. It is normally not greater than the amount of the primary structurant.

The secondary structurants employable herein can be non-polymeric or polymeric. Solid linear fatty alcohol and/ or a wax may be included but are not preferred. In anhydrous compositions notably antiperspirants which are suspension sticks, non-polymeric secondary structurants, sometimes referred to as gellants, can be selected from fatty acids or salts thereof, such as stearic acid or sodium stearate or 12-hydroxy stearic acid. Fatty acids are preferably not used in aqueous sticks, e.g. aqueous emulsion sticks because they can form insoluble precipitates with aluminium ions. Other suitable gellants can comprise dibenzylidene alditols, e.g. dibenzylidene sorbitol. Further suitable gellants can comprise lanosterol, selected N-acyl amino acid derivatives, including ester and amide derivatives, such as N-lauroyl glutamic acid dibutylamide, which gellants can be contemplated in conjunction with 12-hydroxy stearic acid or an ester or amide derivative thereof. Still further gellants include amide derivatives of di or tribasic carboxylic acids, such as alkyl N,N'dialkylsuccinamides, e.g. dodecyl N,N'-dibutylsuccinamide.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. If an aqueous disperse phase is present, polyacrylamides, polyacrylates or polyalkylene oxides may be used to structure or thicken this aqueous phase.

One category of polymer which may be employed as a second structurant for the continuous phase is a polysaccharide esterified with monocarboxylic acid containing at least 8 carbon atoms.

Preferred in this category is a dextrin fatty acid ester having the formula:

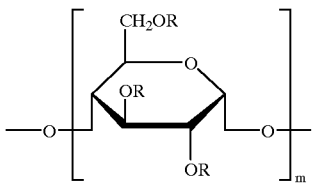

wherein each R group, individually, is a hydrogen or an acyl group of up to 22 carbon atoms, provided that at least one R group per glucose unit is an acyl group of 8 to 22 carbon atoms, and m has a value from about 20 to 30. The dextrin fatty acid ester can be a partial ester, i.e. at least one R group is hydrogen. Another possibility is that the dextrin can be completely esterified with $C_8$ to $C_{22}$ acyl groups, i.e. every R group is a $C_8$–$C_{22}$ acyl group. In preferred embodiments, the degree of substitution with an R group which is a $C_8$–$C_{22}$ alkyl group is at least 2 (i.e., at least two R groups are $C_8$–$C_{22}$ acyl groups). A further possibility would be that some R groups are acyl groups of less than 8 carbon atoms while some R groups (at least one per glucose residue, preferably at least two) is a $C_8$ to $C_{22}$ acyl group. The $C_8$–$C_{22}$ fatty acids that provide acyl groups can be saturated or unsaturated acids.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Mechanical Properties and Product Packages

The compositions of this invention are structured liquids and may be firm or soft in appearance. Even a soft solid has an ability to sustain its own shape, for instance if it is removed from a mould without being subjected to shear it will retain its shape for at least 30 seconds, usually longer.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a hand-wheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9° 10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Texture Analyser

This test apparatus can move a blunt probe into or out from a sample at a controlled speed and at the same time measure the applied force. The parameter which is determined as hardness is a function of the peak force and the projected area of indentation.

A specific test protocol used a Stable Micro systems TA.XT2i Texture Analyser. A metal sphere, of diameter 9.5 mm, was attached to the underside of the Texture Analyser's 5 kg load cell such that it could be used for indenting a sample placed beneath it on the base plate of the instrument. After positioning the sample, the sphere position was adjusted until it was just above the sample surface. Texture Expert Exceed software was used to generate the subsequent motion profile used in the test method. This profile initially indented the sphere into the sample at an indentation speed of 0.05 mm/s until a designated force was reached, which was chosen such that the distance of penetration into the sample was less than the radius of the sphere. At this load the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

Suitable samples for measurement were either contained in stick barrels, which had a screw mechanism (if firm solids), or in 15 ml glass jars (if soft solids). For the barrel samples, the stick was wound up until it protruded above the edges of the barrel and then a knife was used to skim the top of the barrel in such a way as to leave a flat uniform surface. The stick was then pushed back into the barrel as far as possible to minimise any mechanical interference resulting from the compliance of the screw mechanism in the pack. Two indents were generally made either side of the screw. Soft-solid samples in the 15 ml jars needed no surface preparation but only had enough surface area for a single indentation test to be performed.

The data associated with each test were manipulated using standard spreadsheet software and used to calculate the hardness, H, using the following equation:

$$H[N/mm^2] = \frac{F_{max}[N]}{A_p[mm^2]}$$

where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading-force-versus-total-penetration-depth. The initial slope of this unloading data depends on the initial elastic recovery of the sample. The plastic indentation depth is estimated from an intercept between the zero force axis and a straight line drawn at a tangent to the initial part of the unloading slope.

Similar hardness measurements were also done using a desktop Instron Universal Testing Machine (Model 5566) fitted with a 10 N load cell, and the data analysis performed in the same way.

iii) Deposition by Firm Sticks

Another test of the properties of a composition is the amount of the composition which is delivered onto a surface when the composition is drawn across that surface (representing the application of a stick product to human skin). To carry out this test of deposition when the composition is a firm stick, able to sustain its own shape, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined. A specific procedure for such tests of deposition and whiteness applicable to a firm solid stick used apparatus to apply a deposit from a stick onto a substrate under standardised conditions and then measures the mean level of white deposits using image analysis.

The substrates used were:
a: 12×28 cm strip of grey abrasive paper (3M™ P800 WetorDry™ Carborundum paper)
b: 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed. The whiteness of the deposit could subsequently be measured as described at (v) below.

(iv) Deposit of Soft Solid

A procedure for a soft solid composition was as follows. The test substrate was a rectangular strip of black worsted fabric 9 cm by 15 cm. This was placed in an apparatus consisting of a metallic base onto which was hinged a metallic frame defining a rectangular aperture of 5 cm by 9 cm. The test substrate was laid on the base. The hinged frame was placed over the fabric and secured to the base by means of two screws thereby clamping the test substrate in place but exposing an area of 5 cm×9 cm through the aperture.

A sample of soft solid composition in a dispensing container was kept at ambient laboratory temperature (about 20° C.) before it was required for measurement. A portion of the composition was then extruded from the container through the dispensing apertures at one end. A weighted amount (0.51 g) of the extruded composition was spread uniformly across the 5 cm×9 cm area of test substrate enclosed by the frame. Spreading was carried out using a plastic spreading tool. After spreading the sample of composition, the substrate was removed from the apparatus and weighed to check that the mass of applied sample was 0.5±0.01 gms.

(v) Whiteness of Deposit

The deposits from the at test (iii) above, or made as in (iv) above, were assessed for their whiteness after an interval of 24 hours approximately.

This was done using a Sony $XC_{77}$ monochrome video camera with a Cosmicar 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

Preparation

Compositions of this invention can be produced by conventional processes for making cosmetic solids or soft-solids. Such processes involve forming a heated mixture of the composition at a temperature which is sufficiently elevated that all the structurant dissolves, pouring that mixture into a mould, which may take the form of a dispensing container, and then cooling the mixture whereupon the structurant solidifies into a network of fibres extending through the water-immiscible liquid phase.

A convenient process sequence for a composition which is a suspension comprises first forming a solution of the structurant in the water-immiscible liquid. This is normally carried out by agitating the mixture at a temperature sufficiently high that all the structurant dissolves (the dissolution temperature) such as a temperature in a range from 50 to 120° C. Thereafter the particulate constituent, for example particulate antiperspirant active, is blended with the hot mixture. This must be done slowly, or the particulate solid must be preheated, in order to avoid premature gelation. The resulting blend is then introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

In a suitable procedure for making emulsion formulations, a solution of the structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary: antiperspirant actives can sometime be supplied in aqueous solution which can be utilised as is). If possible, this solution of antiperspirant active which will become the disperse phase is preferably heated to a temperature similar to that of the continuous phase with structurant therein, but without exceeding the boiling point of the solution, and then mixed with the continuous phase. Alternatively, the solution is introduced at a rate which maintains the temperature of the mixture. If it is necessary to work at a temperature above the boiling temperature of the disperse phase, or at a temperature where evaporation from this phase is significant, a pressurised apparatus could be used to allow a higher temperature to be reached. With the structurant materials of this invention this is usually unnecessary. After the two phases are mixed, the resulting mixture is filled into dispensing containers, typically at a temperature 5 to 30° C. above the setting temperature of the composition, and allowed to cool as described above for suspension sticks.

EXAMPLES

Example 1

Preparation of 1,2-diamidocyclohexane Compounds

The following general procedure was employed, based on that described by K Hanabusa, M Yamada, M Kimura and H Shirai, in Prominent Gelation and Chiral Aggregation of Alkylamides Derived from Trans-1,2-Diaminocyclohexane, Angew. Chem. Int.Ed. Engl., 35 (17), 1949 (1996).

The reaction vessel was a three necked one liter round bottom flask equipped with overhead mechanical stirrer, water condenser and 250 ml pressure equalising dropping funnel. 1,2-diaminocyclohexane in 300 mls of toluene was placed in the flask followed by triethylamine. The acid chloride in 150 mls of toluene was placed in the pressure equalising funnel. The solution of the amine was taken to reflux after which the acid chloride was added dropwise. A white dense precipitate (triethylamine hydrochloride) forms almost immediately. After 4 hours of reflux the triethylamine hydrochloride is filtered off whilst the reaction mixture is still hot and the toluene is evaporated off under vacuum.

Preparation of trans-(1R,2R)-di-dodecanamido cyclohexane also named as trans N,N'-bis(dodecanoyl)-1R,2R-diaminocyclohexane and here designated as structurant K7. The formula of this material is shown below. The asterisks highlight chiral centres:

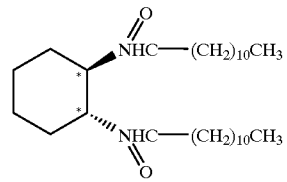

(K7)

This was prepared according to the general reaction method and with the following reagents: (1R,2R)-(−)-1,2-diaminocyclohexane (5 g, 4.38×10$^{-2}$ mol) ex Fluka, lauroyl chloride (19.15 g, 0.87×10$^{-2}$ mol) and triethylamine (19 mls, 0.14 mol). A white solid was obtained after recrystallisation from dichloromethane. The yield was 15.50 g (65%).

Characterisation $^1$H n.m.r. was consistent with required structure.

FT-IR showed ν = 1637 cm$^{-1}$ Amide I (C = O) stretch 1545 cm$^{-1}$ Amide II (NH) deformation 3272 cm$^{-1}$ Amide (NH) stretch Preparation of trans-(1R,2R)-di-octadecanamidocyclohexane also named N,N'-bis (octadecanoyl)-(1R,2R)-trans-diaminocyclohexane and here designated structurant K15. The formula of this compound is shown below. The asterisks highlight chiral centres:

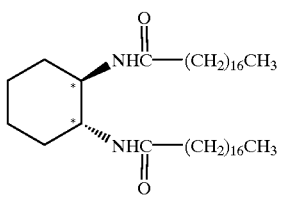

(K15)

This was prepared according to the general reaction method and with the following reagents:

(1R,2R)-(−)-1,2-diaminocyclohexane (2.5 g, 2.19×10$^{-2}$ mol) stearoyl chloride (13.26 g, 4.37×10$^{-2}$ mol) and triethylamine (7 mls, 5.0×10$^{-2}$ mol). A white solid was obtained after recrystallisation from dichloromethane. The yield was 9.67 g (62%).

Characterisation $^1$H n.m.r. was consistent with required structure.

FT-IR showed $v = 1638$ cm$^{-1}$ Amide I $(C = O)$ stretch 1545 cm$^{-1}$ Amide II $(NH)$ deformation 3272 cm$^{-1}$ Amide $(NH)$ stretch Preparation of trans-1,2-di-dodecanamidocyclohexane (not optically active); also named as trans N,N'-bis(dodecanoyl)-1,2-diaminocyclohexane and here referred to as structurant K25, with formula:

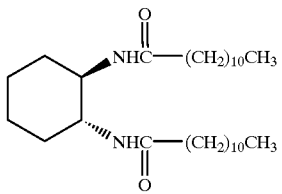

(K25)

This was prepared according to the general reaction method and with the following reagents:

trans-1,2-diaminocyclohexane (4 g, 3.5×10$^{-2}$ mol;) ex Aldrich lauroyl chloride (15.33 g, 7.0×10$^{-2}$ mol) and triethylamine (10 mls, 7.18×10$^{-2}$ mol). A white solid was obtained after recrystallisation from ethanol. The yield was 10.76 g (64%).

Characterisation $^1$H n.m.r. was consistent with required structure.

FT-IR showed $v = 1634$ cm$^{-1}$ Amide I $(C = O)$ stretch 1540 cm$^{-1}$ Amide II $(NH)$ deformation 3294 and 3260 cm$^{-1}$ Amide $(NH)$ stretch Preparation of cis/trans-1,2-di-dodecanamidocyclohexane also named as N,N'-bis(dodecanoyl)-1,2-diaminocyclohexane (not optically active; cis/trans mixture). Here it is referred to as structurant K26, having formula:

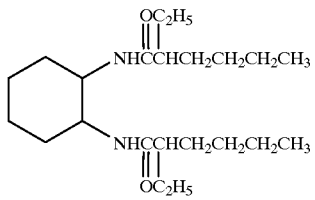

(K26)

This was prepared according to the general reaction method and with the following reagents:

1,2-diaminocyclohexane (4 g, 3.5×10$^{-2}$ mol) ex Aldrich, lauroyl chloride (15.33 g, 7.0×10$^{-2}$ mol) and triethylamine (10 mls, 7.18×10$^{-2}$ mol). A white fibrous material was obtained after recrystallisation from ethanol. The yield was 6.37 g (38%).

Characterisation $^1$H n.m.r was consistent with required structure.

FT-IR showed $v = 1634$ cm$^{-1}$ Amide I $(C = O)$ stretch 1541 cm$^{-1}$ Amide II $(NH)$ deformation 3294 and 3258 cm$^{-1}$ Amide $(NH)$ stretch Preparation of cis/trans-1,2-di-(2-ethylhexan amido) cyclohexane also named as N,N'-bis(2-ethylhexanoyl)-1,2-diaminocyclohexane (not optically active; cis/trans mixture). Here it is designated structurant K40. It has the formula:

(K40)

NHCCHCH$_2$CH$_2$CH$_2$CH$_3$
            ‖
           OC$_2$H$_5$ (structure with cyclohexane bearing two NHCCHCH$_2$CH$_2$CH$_2$CH$_3$ / OC$_2$H$_5$ groups)

This was prepared according to the general reaction method and with the following reagents:

1,2-diaminocyclohexane (4 g, 3.5×10$^{-2}$ mol) ex Aldrich, 2-ethylhexanoyl chloride (11.39 g, 7.0×10$^{-2}$ mol) and triethylamine (9.75 mls, 6.99×10$^{-2}$ mol). A white solid was obtained after recrystallisation from ethyl acetate and hexane. The yield was 4.02 g (31.31%).

Characterisation

Mpt: 225–228° C.

$^1$H n.m.r. was consistent with required structure

FT-IR $v = 1633$ cm$^{-1}$ Amide I $(C = O)$ stretch 1535 cm$^{-1}$ Amide II $(NH)$ deformation 3274 and 3258 cm$^{-1}$ Amide $(NH)$ stretch Preparation of a 1,3-cyclohexane Derivative The compound 1,3-cyclohexanebis(methyldodecylamide), also named N-[3-(dodecanamidomethyl)-cyclohexylmethyl]dodecanamide or N,N-bis-(dodecanoyl-1,3-(methylamino)cyclohexane, and referred to here as structurant K19 was prepared by the general reaction method. The reaction and product were as follows:

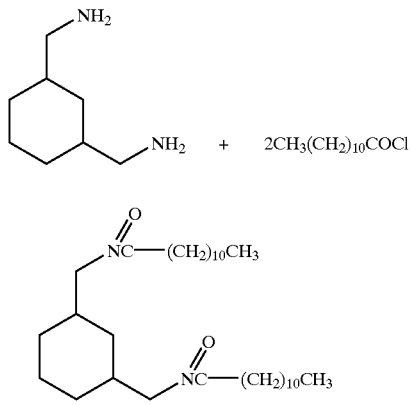

(K19)

The reagents were: 1,3-cyclohexanebis(methylamine), (10 g, 7.03×10$^{-2}$ mol) and lauroyl chloride (30.76 g, 14.06×10$^{-2}$ mol).

The reaction was carried out by heating in the presence of triethylamine with toluene as solvent. A white solid was obtained after recrystallisation from dichloromethane. The yield was 21.04 g (59%).
Characterisation
Mpt: 126–129° C.
$^1$H n.m.r. was consistent with required structure.

FT-IR showed $v = 1635$ cm$^{-1}$ Amide I ($C = O$) stretch 1545 cm$^{-1}$ Amide II ($NH$) deformation 3277 cm$^{-1}$ Amide ($NH$) stretch

Example 2

A number of suspension stick compositions, as set out in the tables below were prepared. The materials used, and their proprietary names, were as follows:

1) Volatile cyclic silicone (cyclomethicone) DC 245 (Dow Corning)
2) Polypropyleneglycol 14 butylether (Fluid AP from Union Carbide)
3) Polydecene (Silkflo 364 NF from Albemarle)
4) Isostearyl alcohol (abbreviated to ISA—Prisorine 3515 from Unichema)
5) C$_{12-15}$ alkyl benzoate (Finsolv TN from Finetex)
6) Al/Zr Tetrachlorohydrex glycine complex (AZAG—7167 from Summit).
7) 12-hydroxystearic acid (Caschem)

The method of preparation was as follows:
The liquids and the structurant(s) were first mixed together in a flask and heated to just above the dissolution temperature of the structurant(s). Gentle stirring was provided with a Hydolph mixer. Once all the structurant was dissolved the antiperspirant active was added and the whole mixture cooled to 5–10° C. above the gelling point determined in a preliminary trial. The mixture was then poured into stick barrels and cooled at room temperature. Penetrometer and whiteness measurements as described above were performed after the sticks had been stored at room temperature for at least 24 hours.

Formulations and measured properties are given in the following tables, in which the amounts of the materials are percentages by weight.

|  | Parts by weight | | | | | | |
|---|---|---|---|---|---|---|---|
|  | 2.1 | 2.2 | 2.3 | 2.4 | 2.5 | 2.6 | 2.7 |
| Formulation no: | | | | | | | |
| DC 245 (1) | 51.4 | 45.9 | 51.4 | 34.3 | 34.3 | 34.3 | 22.8 |
| Fluid AP (2) | — | 11.3 | 17.1 | — | 17.6 | 34.3 | 22.4 |
| Silkflo 364 NF (3) | 17.1 | 11.3 | — | 34.3 | 17.6 | — | 22.8 |
| AZAG 7167 (6) | 24.0 | 24.0 | 24.0 | 24.0 | 24.0 | 24.0 | 24.0 |
| K26 | 2.5 | 2.5 | 2.5 | 2.5 | 2.5 | 2.5 | 2.5 |
| 12 HSA (7) | 5.0 | 5.0 | 5.0 | 5.0 | 5.0 | 5.0 | 5.0 |
| Evaluation | | | | | | | |
| Hardness (mm) | 14.3 | 23.2 | 19.2 | 10.8 | 19.3 | 18.2 | 21.0 |
| Whiteness on grey paper after 24 hours | 85 | 55 | 39 | 40 | 33 | 33 | 33 |
| Whiteness on black wool after 24 hours | 56 | 43 | 26 | 42 | 29 | 15 | 13 |

|  | 2.8 | 2.9 | 2.10 | 2.11 | 2.12 | 2.13 | 2.14 |
|---|---|---|---|---|---|---|---|
| Formulation no: | | | | | | | |
| DC 245 (1) | 11.3 | 11.3 | 53.3 | 47.6 | 25.5 | 35.5 | 35.5 |
| Fluid AP (2) | 11.3 | 45.9 | — | 11.7 | — | 17.8 | 35.5 |
| Silkflo 364 NF (3) | 45.9 | 11.3 | 17.8 | 11.7 | 35.5 | 17.8 | — |
| AZAG 7167 (6) | 24.0 | 24.0 | 24.0 | 24.0 | 24.0 | 24.0 | 24.0 |
| K26 | 2.5 | 2.5 | 2.5 | 2.5 | 2.5 | 2.5 | 2.5 |
| 12 HSA (7) | 5.0 | 5.0 | — | — | — | — | — |
| Evaluation | | | | | | | |
| Hardness (mm) | 16.6 | 20.9 | 21.2 | 20.9 | 15.4 | 21.0 | 19.5 |
| Whiteness on grey paper after 24 hours | 38 | 38 | 54 | 27 | 27 | 26 | 36 |
| Whiteness on black wool after 24 hours | 24 | 15 | 45 | 29 | 18 | 28 | 42 |

As a comparison, a conventional white antiperspirant stick structured with fatty alcohol and castor wax gave whiteness values of:

| | |
|---|---|
| Whiteness on grey paper after 24 hours | 118 |
| Whiteness on black wool after 24 hours | 186 |

|  | Parts by weight | | | | | | |
|---|---|---|---|---|---|---|---|
|  | 2.15 | 2.16 | 2.17 | 2.18 | 2.19 | 2.20 | 2.21 | 2.22 |
| Formulation no: | | | | | | | | |
| DC 245 (1) | 23.7 | 11.7 | 11.7 | 53.3 | 35.5 | 34.3 | 34.3 | 35.5 |
| Fluid AP (2) | 23.7 | 11.7 | 47.6 | 17.8 | — | 34.3 | — | — |
| Silkflo 364 NF (3) | 23.7 | 47.6 | 11.7 | — | — | — | — | — |
| Finsolv TN (5) | — | — | — | — | 35.5 | — | 34.3 | — |
| ISA (4) | — | — | — | — | — | — | — | 35.5 |
| AZAG 7167 (6) | 24.0 | 24.0 | 24.0 | 24.0 | 24.0 | 24.0 | 24.0 | 24.0 |
| K26 | 5.0 | 5.0 | 5.0 | 5.0 | — | — | — | — |
| K7 | — | — | — | — | 5.0 | — | — | — |
| K25 | — | — | — | — | — | 2.5 | — | — |
| K40 | — | — | — | — | — | — | 2.5 | — |

-continued

| | Parts by weight | | | | | | | |
|---|---|---|---|---|---|---|---|---|
| | 2.15 | 2.16 | 2.17 | 2.18 | 2.19 | 2.20 | 2.21 | 2.22 |
| K15 | — | — | — | — | — | — | — | 5.0 |
| 12 HSA (7) | — | — | — | — | — | 5.0 | 5.0 | — |
| Evaluation | | | | | | | | |
| Hardness (mm) | 14.8 | 13.7 | 16.5 | 22.3 | 18.7 | 19.9 | 11.3 | 20.7 |
| Whiteness on grey paper after 24 hours | 32 | 22 | 32 | 57 | 27 | 25 | 27 | 31 |
| Whiteness on black wool after 24 hours | 33 | 21 | 33 | 45 | 28 | 12 | 13 | 22 |

Example 3

Emulsion Sticks

A number of emulsion stick compositions were prepared. Some of the materials used were listed at the beginning of Example 2. Others were 8) Cetyl dimethicone copolyol (Abil EM90 emulsifier from Th. Goldschmidt)

9) 50% aqueous solution of Al/Zr pentachlorohydrate (Zirkonal 50 from Giulini)

The liquids and emulsifier were mixed together in a beaker and heated to 5–10° C. above the dissolution temperature of the amido-containing structurant, while gently stirring with a Silverson head. The structurant was added. Next the antiperspirant active phase, preheated to the same temperature, was added slowly. During this addition, the stirring was increased to 8000 rpm. Once the addition was complete the mixture was stirred for a further 5 minutes at 8000 rpm without any cooling. The process was then stopped and the mixture transferred into stick barrels and left at room temperature to cool.

| | Parts by weight | | | | | | |
|---|---|---|---|---|---|---|---|
| | 3.1 | 3.2 | 3.3 | 3.4 | 3.5 | 3.6 | 3.7 |
| Formulation no: | | | | | | | |
| DC 245 (1) | 7.3 | 14.7 | 7.3 | 22.0 | 22.0 | 29.5 | 22.0 |
| Fluid AP (2) | 7.3 | 14.7 | 29.5 | 11.0 | 22.0 | 7.3 | — |
| Silkflo 364 NF (3) | 29.5 | 14.7 | 7.3 | 11.0 | — | 7.3 | 22.0 |
| Abil EM 90 (8) | 1.0 | 1.0 | 1.0 | 1.0 | 1.0 | 1.0 | 1.0 |
| Zirconal 50 (9) | 50.0 | 50.0 | 50.0 | 50.0 | 50.0 | 50.0 | 50.0 |
| K26 | 5.0 | 5.0 | 5.0 | 5.0 | 5.0 | 5.0 | 5.0 |
| Evaluation | | | | | | | |
| Hardness (mm) | 17.4 | 29.1 | 17.5 | 19.3 | 14.0 | 14.1 | 14.5 |
| Whiteness on grey paper after 24 hours | 27 | 31 | 34 | 31 | 29 | 26 | 27 |
| Whiteness on black wool after 24 hours | 20 | 83 | 30.0 | 18 | 14 | 21 | 13 |

Example 4

Soft Solid Suspensions

A number of soft solid suspension compositions were prepared using materials listed at the beginning of Example 2. Also used was 10) Octyldodecanol (Eutanol G from Henkel/Cognis)

The procedure was as follows:

A solution of the structurant(s) in the organic liquid(s) was made by mixing these materials, heating and agitating the mixture at a temperature sufficiently high that the structurant (s) dissolve. The mixture was then allowed to cool to 80–85° C. before the aluminium antiperspirant active was added. The mixture was then allowed to cool to 5–20° C. above its gelling temperature (determined in a preliminary experiment) and introduced into dispensing containers for soft solids. These were then left to cool to room temperature.

Hardness was determined by texture analyser as described earlier. Deposits on black fabric were made, and their whiteness determined, by the procedures given earlier.

The formulations and the measurement results are given in the following table:

| | 4.1 | 4.2 | 4.3 | 4.4 |
|---|---|---|---|---|
| Formulation No | Parts by weight | | | |
| K19 | 5 | 5 | 3 | 3 |
| 12-HSA (7) | — | 5 | 3 | 3 |
| Cyclomethicone (1) | 34.25 | 31.75 | 33.75 | 32.75 |
| Octyldodecanol (10) | 34.25 | 31.75 | 33.75 | 32.75 |
| AZAG 7167 (6) | 26.5 | 26.5 | 26.5 | 26.5 |
| Evaluation | | | | |
| Hardness (N/mm²) | 0.018 | 0.079 | 0.033 | 0.081 |
| Whiteness measurement (1 h) | 13 | 17 | 18 | 16 |
| Whiteness measurement (24 h) | 11 | 13 | 13 | 13 |

We claim:

1. An antiperspirant composition comprising:

(i) a continuous phase which comprises water-immiscible liquid carrier, (ii) a structurant therein which is at least one amido-containing compound of the general formula

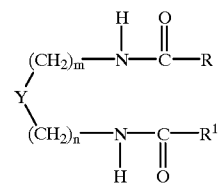

wherein R and $R^1$ each independently denote an organic moiety of 5 to 27 carbon atoms, m and n are independently 0 or 1, Y is a cyclohexane ring bearing the amido-containing substituent groups

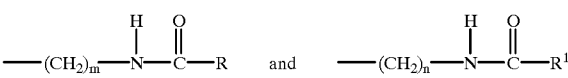

in 1,2 or 1,3 positions; and (iii) an antiperspirant active material.

2. A composition according to claim 1 wherein R and $R^1$ are the same.

3. A composition according to claim 1 wherein Y denotes 1,2-cyclohexane.

4. A composition according to claim 1 wherein R and $R^1$ are the same and Y denotes 1,2-cyclohexane.

5. A composition according to claim 4 wherein m and n are zero, so that the amido-containing structurant compound has general formula

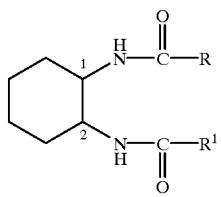

6. A composition according to claim 3 wherein the amido-containing structurant has trans stereochemistry.

7. A composition according to claim 6 wherein the amido-containing structurant is optically active.

8. A composition according to claim 6 wherein the amido-containing structurant is a cis/trans mixture.

9. A composition according to claim 1 wherein Y denotes 1,3-cyclohexane.

10. A composition according to claim 9 wherein m and n are both 1.

11. A composition according to claim 1 characterised in that the water-immiscible liquid carrier contains a volatile silicone and optionally a non-volatile silicone and/or a non-silicone hydrophobic organic liquid selected from hydrocarbons, hydrophobic aliphatic esters, aromatic esters, hydrophobic alcohols and hydrophobic ethers.

12. A composition according to claim 1 wherein the water-immiscible carrier liquid contains silicone oil in an amount which is at least 10% by weight of the composition.

13. A composition according to claim 1 containing from 0.1 to 15% by weight of the amido-containing structurant.

14. A composition according to claim 1 which contains not more than 5% by weight of any fatty alcohol which is solid at 20° C.

15. A composition according to claim 13 which does not contain more than 3% of any material which is solid at 30° C., is molten at 95° C. and soluble in the water-immiscible liquid at 95° C., but does not form a network of fibres in the water-immiscible liquid.

16. A composition according to claim 1 wherein the composition is an emulsion with the antiperspirant active in solution in a hydrophilic, preferably water-miscible, disperse phase.

17. A composition according to claim 16 wherein the disperse phase contains a diol or polyol.

18. A composition according to claim 17 wherein the disperse phase contains glycerol or 1,2-propane diol.

19. A composition according to claim 16 which contains from 0.1% to 10% by weight of a nonionic emulsifier.

20. A composition according to claim 16 which does not contain more than 8% by weight of ethanol or any monohydric alcohol with a vapour pressure above 1.3 kPa at 22° C.

21. A composition according to claim 1 wherein the composition is a suspension with a particulate antiperspirant active dispersed in said liquid continuous phase.

22. A composition according to claim 1 wherein the antiperspirant active comprises an aluminium and/or zirconium halohydrate, an activated aluminium and/or zirconium halohydrate, or an aluminium and/or zirconium complex or an activated aluminium and/or zirconium complex.

23. A composition according to claim 22 which is a halohydrate or complex in which aluminium and zirconium are both present.

24. A composition according to claim 22 wherein the proportion of antiperspirant active is from 5 to 40% by weight of the composition.

25. An antiperspirant product comprising a dispensing container having at least one aperture for delivery of the contents of the container, means for urging the contents of the container to the said aperture or apertures, and a composition according to claim 1 accommodated within the container.

26. A product according to claim 25 wherein the composition is in the form of a stick and the container has an open end at which an end portion of the stick of composition is exposed for use.

27. A product according to claim 26 wherein the composition is a firm gel such that a penetrometer needle with a cone angle of 9 degrees 10 minutes, drops into the gel for no more than 30 mm when allowed to drop under a total weight of 50 grams for 5 seconds.

28. A product according to claim 25 wherein the composition is a soft solid and the said aperture or apertures have smaller overall cross section than the container.

29. A process for the production of a composition according claim 1 comprising, not necessarily in any order, the steps of incorporating into a water-immiscible liquid carrier a structurant which is one or more amido structurant compounds as defined above, mixing the liquid carrier with a particulate solid antiperspirant active or a solution of antiperspirant active to be suspended therein, heating to an elevated temperature at which the structurant is in solution in the water-immiscible liquid carrier, followed by cooling or permitting the mixture to cool to a temperature at which it is thickened or solidified.

30. A process according to claim 26 which includes a step of pouring the mixture at elevated temperature into a dispensing container and allowing it to cool therein so as to produce a product.

31. A cosmetic method for preventing or reducing perspiration on human skin comprising topically applying to the skin a composition according to claim 1.

32. A method according to claim 31 in which the composition contains from 5 to 40% by weight of an antiperspirant active which comprises an aluminium and/or zirconium halohydrate, an activated aluminium and/or zirconium halohydrate, or an aluminium and/or zirconium complex or an activated aluminium and/or zirconium complex.

* * * * *